United States Patent [19]
Blaney et al.

[11] Patent Number: 5,714,142
[45] Date of Patent: Feb. 3, 1998

[54] METHOD AND COMPOSITIONS FOR INCREASING THE SERUM HALF-LIFE OF PHARMACOLOGICALLY ACTIVE AGENTS BY BINDING TO TRANSTHYRETIN-SELECTIVE LIGANDS

[76] Inventors: Jeffrey M. Blaney, 6601 Saroni Dr., Oakland, Calif. 94611; Fred Cohen, 767 Rhode Island, San Francisco, Calif. 94107

[21] Appl. No.: 664,372

[22] Filed: Jun. 13, 1996

Related U.S. Application Data

[63] Continuation of Ser. No. 200,387, Feb. 23, 1994, abandoned.

[51] Int. Cl.$^6$ ............................................. A61K 47/48
[52] U.S. Cl. .................... 424/85.2; 424/85.4; 514/11; 514/16; 514/262; 514/274; 514/335; 514/368; 514/421; 514/423; 514/460; 514/471; 514/567; 514/568; 514/571; 514/620; 514/626; 514/737; 514/772; 514/776
[58] Field of Search ....................... 424/85.2, 85.4; 514/776, 772, 11, 16, 262, 274, 335, 368, 421, 423, 460, 471, 567, 568, 571, 620, 626, 737

[56] References Cited

U.S. PATENT DOCUMENTS

| | | | |
|---|---|---|---|
| 5,068,227 | 11/1991 | Weinshenker | 514/58 |
| 5,273,885 | 12/1993 | Visor et al. | 435/7.93 |

FOREIGN PATENT DOCUMENTS

| | | |
|---|---|---|
| 2 085 160 | 4/1982 | United Kingdom. |
| WO91/01743 | 2/1991 | WIPO. |

OTHER PUBLICATIONS

Bickel et al., "Pharmacologic effects in vivo in brain by vector–mediated peptide drug delivery," *Proc. Natl. Acad. Sci., USA* 90:2618–2622 (1993).
Brouwer et al., "Competitive inhibition of thyroxine binding to transthyretin by monohydroxy metabolites of 3,4,3', 4'-tetrachlorobiphenyl," *Chemosphere* 20(7–9):1257–1262 (1990).
Cavalieri et al., "The effects of drugs on the distribution and metabolism of thyroid hormones," *Pharmacological Reviews* 33(2):55–80 (1981).
Divino et al., "Receptor–mediated uptake and internalization of transthyretin," *J. Biol. Chem.* 265(3):1425–1429 (1990).
Divino et al., "Transthyretin Receptors on Human Astrocytoma Cells," *J. Clin. Endocrin. Metab.* 71(5):1265–1268 (1990).
Edgington et al., "The anatomy of access: Peptide drug delivery," *Bio/Technology* 9:1327–1331 (Dec. 1991).
Leamon et al., "Delivery of macromolecules into living cells: A method that exploits folate receptor endocytosis," *Proc. Natl. Acad. Sci., USA* 88:5572–5576 (1991).
Mao et al., "Superoxide dismutase: Improving its pharmacological properties by conjugation with human serum albumin," *Biomat., Art. Cells, Art. Org.* 17:229–244 (1989).

Munro et al., "Drug competition for thyroxine binding to transthyretin (prealbumin): Comparison with effects on thyroxine–binding globulin," *J. Clin. Endocrin. Metabol.* 68(6):1141–1147 (1989).
Ogino, "Chemical modification of superoxide dismutase," *Int. J. Peptide Protein Res.* 32:153–159 (1988).
Van Den Berg, "Interaction of chlorinated phenols with thyroxine binding sites of human transthyretin, albumin and thyroid binding globulin," *Chem.–Biol. Interactions* 76:63–75 (1990).
Arano et al., "A Novel Bifunctional Metabolizable Linker for the Conjugation of Antibodies with Radionuclides," *Bioconjugate Chem.* 2:71–76 (1991).
Bank, "Effects of Polyhalogenated Aromatic Hydrocarbons on Vitamin A Catabolism and the Regulation of Vitamin A Homeostatis in Rats (Hydrocarbons)," *Database: Dissertation Abstracts* AN:AAI9013852 (1989).
Bhattacharya et al., "Homogeneous Enzyme Immunoassay of Thyroxine and Triiodothyronine Using Glucose–6–phosphate Dehydrogenase and Horse Radish Peroxidase," *Indian Journal of Experimental Biology* 26:990–992 (1988).
Blondeau et al., "Characterization of the Thyroid Hormone Transport System of Isolated Hepatocytes," *The Journal of Biological Chemistry* 263(6):2685–2692 (1988).
Busche et al., "Preparation and Utility of a Radioiodinated Analogue of Daunomycin in the Study of Multidrug Resistance," *Mol. Pharmacol.* 35(4): 414–421 (1989).
McKinney et al., "Molecular Interactions of Toxic Chlorinated Dibenzo–p–dioxins and Dibenzofurans with Thyroxine Binding Prealbumin," *J. Med. Chem.* 28:375–381 (1985).
Melhus, "Studies of the Vitamin A Transporting Protein Complex Retinol–Binding Protein—Transthyretin," *Database: Dissertation Abstracts* AN: AAIC220221 (1990).
Nichols, "Molecular Genetic Studies of Autosomal Dominant, Systemic Amyloidosis (Amyloidosis)," *Database: Disssertation Abstracts* AN: AAI9020740 (1989).
Place et al., "A Colorimetric Immunoassay Based on an Enzyme Inhibitor Method," *J. Immunol. Methods* 61(2):209–216 (1983).
van den Berg et al., "A New Radioimmunoassay for the Determiniation of the Angiotensin–converting Enzyme Inhibitor Perindopril and its Active Metabolite in Plasma and Urine: Advantages of a Lysine Derivative as Immunogen to Improve the Assay Specificity," *J. Pharm. Biomed. Anal.* 9(7):517–524 (1991).

*Primary Examiner*—S. Mark Clardy
*Attorney, Agent, or Firm*—Dianne E. Reed; Kenneth M. Goldman; Robert P. Blackburn

[57] ABSTRACT

Compositions and methods are provided for increasing the serum half-life of a pharmacologically active agent. The novel compositions are covalent conjugates of the selected pharmacologically active agent and a transthyretin-binding ligand such as tetraiiodothyroacetic acid, 2,4,6-triiodophenol, flufenamic acid, or the like.

27 Claims, No Drawings

1

METHOD AND COMPOSITIONS FOR INCREASING THE SERUM HALF-LIFE OF PHARMACOLOGICALLY ACTIVE AGENTS BY BINDING TO TRANSTHYRETIN-SELECTIVE LIGANDS

This application is a continuation of application Ser. No. 08/200,387 filed on Feb. 23, 1994, abandoned.

TECHNICAL FIELD

The invention relates generally to methods and compositions for increasing the serum half-life of peptides, proteins, nucleotides, oligonucleotides, oligosaccharides and other drug molecules. More specifically, the invention concerns pharmaceutical compositions comprising covalent conjugates of pharmacologically active agents with transthyretin-selective ligands, and to related methods of use.

BACKGROUND

The tremendous potential for exploiting the highly potent and specific biological activities of peptides, proteins, oligonucleotides and other drugs has not been fulfilled due to their general lack of oral bioavailability (typically less than 5%), short half-lives (often less than five minutes), and limited ability to penetrate cell membranes and, for CNS-active peptides, the blood-brain barrier. For acute indications and indications where no oral therapy is available, drug delivery may be effected by way of injection, but other problems still persist.

It is clearly desirable to extend the serum half-life of certain drugs so that their therapeutic potential may be realized without need for frequent administration and/or high dosages. In this regard, one approach has been to conjugate small molecule drugs, peptides or proteins to a large, stable protein which is too large to be filtered through the kidneys (e.g., serum albumin, or "SA") and therefore has a long half-life. For example, the five-minute half-life of superoxide dismutase ("SOD") increases to five to six hours upon covalent conjugation to SA (G. D. Mao et al., "Superoxide dismutase: Improving its pharmacological properties by conjugation with human serum albumin," *Biomat., Art. Cells, Art. Org.* 17:229–244 (1989)). Another approach has been to use endogenous receptor-mediated endocytosis systems to deliver drugs across membranes into target cells by covalently conjugating the drug to the ligand for the transport system (C. P. Leamon et al., "Delivery of macromolecules into living cells: A method that exploits folate receptor endocytosis," *Proc. Natl. Acad. Sci., U.S.A.* 88:5572–5576 (1991)). Using this approach, uptake of several different folate-linked proteins by cultured cells was demonstrated. Additionally, Bickel et al. (U. Bickel et al., "Pharmacologic effects in vivo in brain by vector-mediated peptide drug delivery," *Proc. Natl. Acad. Sci., U.S.A.* 90:2618–2622 (1993)) biotinylated a vasoactive intestinal peptide ("VIP") analog and formed a complex of the biotinylated VIP with a covalent conjugate of avidin and the OX26 monoclonal antibody to the transferrin receptor. The VIP-avidin-antibody complex successfully crossed the blood-brain barrier in rats after injection due to transferrin receptor-mediated endocytosis on the cells lining the barrier. All of these approaches focus on covalent attachment of a small molecule, peptide or protein drug to an exogenous carrier protein, resulting in a macromolecular complex that is far too large to be orally absorbed and that must instead be administered by injection. Additionally, with the exception of the Mao et al. work, these approaches, although illustrating the use of drug "tagging" in facilitating drug delivery, do not provide a way to increase the serum half-life of the drug administered.

The present approach addresses the aforementioned need in the art in that methods and compositions are herein provided which increase the serum half-life of peptides, proteins, nucleotides, oligonucleotides, oligosaccharides and other drug molecules. The invention involves the exploitation of an endogenous plasma protein, transthyretin ("TTR," also known as prealbumin) by endowing the drug to be administered with functionality that allows it to bind specifically to the protein. As is well known, transthyretin is one of three major plasma transport proteins for the thyroid hormones $T_3$ (triiodothyronine), $T_4$ (tetraiodo-thyronine or thyroxine), along with serum albumin ("SA") and thyroid-binding globulin ("TBG").

It has now been found that covalent attachment of a peptide, protein, nucleotide, oligonucleotide, oligosaccharide or other drug to a transthyretin-selective ligand, as described and claimed herein, will reversibly bind the drug to TTR with a $K_d$ in the range of approximately $10^{-5}$ to $10^{-10}$ M, which in turn greatly reduces renal excretion and increases serum half-life. The pharmacokinetic properties of these conjugates are believed to be similar, in most cases, to those of transthyretin (which has a $t_{1/2}$ of up to about two days) or $T_4$ (which has a $t_{1/2}$ of up to about six to seven days); however the intrinsic activity of the drug is not adversely affected, and cellular or blood-brain penetration may be facilitated. The drug-TTR conjugate may also be resistant to protease activity and other metabolic degradation. TTR-binding ligands are small (typically having a molecular weight of less than about 500), so the resulting drug-TTR ligand conjugate will still be small enough to be orally absorbed.

RELATED ART

In addition to the references cited in the preceding section, the following publications are of interest with respect to the present invention:

S. M. Edgington et al., "The anatomy of access: Peptide drug delivery," *Bio/Technology* 9:1327–1331 (December 1991), which provides an overview of the problems involved in the delivery of peptide drugs and some of the approaches which have been taken to address those problems;

P. Chris de Smidt et al., "Association of antisense oligonucleotides with lipoproteins prolongs the plasma half-life and modifies the tissue distribution," *Nuc. Acids. Res.* 19(17):4695–4700 (1991), in which high-density lipoproteins, low-density lipoproteins, and albumin are evaluated as possible transport vehicles to deliver cholesterol-derivatized antisense oligonucleotides and increase the serum half-life thereof;

T. Ogino, "Chemical modification of superoxide dismutase," *Int. J. Peptide Protein Res.* 32:153–159 (1988), which describes modifying superoxide dismutase by covalently linking lysyl residues to poly-(styrene-co-maleic acid) butyl ester through amide linkages, a modification noted to extend the half-life of the enzyme;

R. R. Cavalieri et al., "The effects of drugs on the distribution and metabolism of thyroid hormones," *Pharmacological Reviews* 33(2):55–80 (1981), which discusses the effect of several drugs, including phenytoin, carbamazepine, phenobarbital, heroin, methadone, methylphenidate, and lithium, on the binding of the thyroid hormones L-thyroxine, $T_4$ and $T_3$ to plasma binding proteins and tissues;

S. L. Munro et al., "Drug competition for thyroxine binding to transthyretin (prealbumin): Comparison with effects on thyroxine-binding globulin," *J. Clin. Endocrin. Metabol.* 68(6):1141–1147 (1989), which evaluates the effects of a number of anthranilic acid-type drugs (e.g., flufenamic, meclofenamic and mefenamic acids) on the binding of $T_4$ to transthyretin and TBG;

K. J. Van Den Berg, "Interaction of chlorinated phenols with thyroxine binding sites of human transthyretin, albumin and thyroid binding globulin," *Chem.-Biol. Interactions* 76:63–75 (1990), which evaluates the possible binding of hydroxylated chlorinated aromatic compounds such as 2,3-dichlorobenzene and 3,4,3',4'-tetrachlorobiphenyl to the $T_4$ binding site of TTR;

A. Brouwer et al., "Competitive inhibition of thyroxine binding to transthyretin by mono-hydroxy metabolites of 3,4,3'4'-tetrachlorobiphenyl," *Chemosphere* 20(7–9):1257–1262 (1990), which evaluates the inhibition of $T_4$-binding to TTR by monohydroxy-metabolites of 3,4,3',4'-tetrachlorobiphenyl;

C. M. Divino et al., "Receptor-mediated uptake and internalization of transthyretin," *J. Biol. Chem.* 265(3):1425–1429 (1990), which presents a study of the effect of TTR on the cellular uptake of $T_4$, and suggests the existence of high affinity, limited capacity TTR binding and internalization sites on hepatocytes and other cells;

C. M. Divino et al., "Transthyretin Receptors on Human Astrocytoma Cells," *J. Clin. Endocrin. Metab.* 71(5):1265–1268 (1990), in which it is demonstrated that transthyretin binds to specific high affinity sites on human astrocytoma cells; and PCT Publication No. WO91/01743, which relates to complexes of biologically active proteins or peptides that are stated to have improved stability in vivo.

SUMMARY OF THE INVENTION

Accordingly, it is a primary object of the invention to address the above-mentioned need in the art by providing a means for increasing the serum half-life of selected pharmacologically active agents.

It is another object of the invention to provide a pharmaceutical composition comprising a selected pharmacologically active agent covalently bound to a transthyretin-selective ligand.

It is still another object of the invention to provide such a composition in which the pharmacologically active agent is a peptide drug.

It is yet another object of the invention to provide a method for adjusting the serum half-life of a pharmacologically active agent which involves administering the agent in the form of a conjugate wherein the agent is bound through a covalent linkage to a transthyretin-selective ligand, and wherein serum half-life is determined by the affinity of the ligand for transthyretin.

It is a further object of the invention to provide a method for extending the serum half-life of a pharmacologically active agent which involves administering the agent in the form of a conjugate wherein the agent is bound through a covalent linkage to a transthyretin-selective ligand whose binding affinities for thyroid-binding globulin and thyroid hormone receptor are each less than about 1% that of the binding affinity of the ligand for transthyretin.

Additional objects, advantages and novel features of the invention will be set forth in part in the description which follows, and in part will become apparent to those skilled in the art upon examination of the following, or may be learned by practice of the invention.

In one aspect, then, a novel pharmaceutical composition is provided in the form of a covalent conjugate of a selected pharmacologically active agent and a selective transthyretin binding ligand. The pharmacologically active agent is a peptide, protein, oligonucleotide or other drug as will be described below, while the transthyretin-selective ligand is selected such that its binding affinities for thyroid-binding globulin and thyroid hormone receptor are each less than about 1% that of the binding affinity of the ligand for transthyretin.

In other aspects, the invention provides methods for adjusting, and preferably extending, the serum half-life of a pharmacologically active agent, which involve preparation and administration of covalent conjugates of the selected pharmacologically active agent and a transthyretin-selective ligand.

DETAILED DESCRIPTION OF THE INVENTION

Definitions

Before the present compositions and methods are disclosed and described, it is to be understood that this invention is not limited to specific drugs, transthyretin-selective ligands, pharmaceutical carriers, or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a pharmacologically active agent" includes mixtures of pharmacologically active agents, reference to "a transthyretin-selective ligand" includes mixtures of two or more such ligands, and the like.

In describing and claiming the present invention, the following terminology will be used in accordance with the definitions set out below.

By the term "pharmacologically active agent" or "drug" as used herein is meant any chemical material or compound suitable for administration to a mammalian, preferably human, individual, which induces a desired local or systemic effect. In general, this includes: anorexics; anti-infectives such as antibiotics and antiviral agents, including many penicillins and cephalosporins; analgesics and analgesic combinations; antiarrhythmics; antiarthritics; antiasthmatic agents; anticholinergics; anticonvulsants; antidiabetic agents; antidiarrheals; antihelminthics; antihistamines; antiinflammatory agents; antimigraine preparations; antinauseants; antineoplastics; antiparkinsonism drugs; antipruritics; antipsychotics; antipyretics; antisense agents; antispasmodics; cardiovascular preparations including calcium channel blockers and beta-blockers such as pindolol; antihypertensives; central nervous system stimulants; cough and cold preparations, including decongestants; diuretics; gastrointestinal drugs, including $H_2$-receptor antagonists; sympathomimetics; hormones such as estradiol and other steroids, including corticosteroids; hypnotics; immunosuppressives; muscle relaxants; parasympatholytics; psychostimulants; sedatives; tranquilizers; and vasodilators including general coronary, peripheral and cerebral; xanthine derivatives.

The terms "peptide," "polypeptide" and "protein" to describe certain pharmacologically active agents useful herein are used interchangeably to mean a naturally occurring, recombinantly produced or chemically synthesized polymer of amino acids. The terms are intended to include peptides containing as few as two amino acids, glycosylated or otherwise modified polypeptides, muteins, fusion proteins, and the like. Preferred peptide drugs for use in conjunction with the present invention have a molecular weight of less than about 50 kD.

As used herein, the terms "oligonucleotide" and "polynucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones (e.g., protein nucleic acids and synthetic sequence-specific nucleic acid polymers commercially available from the Anti-Gene Development Group, Corvallis, Oreg., as Neugene™ polymers), providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. Generally, oligonucleotide and polynucleotide drugs, as used in conjunction with the invention, contain about 10 to 30 nucleotides.

An "effective amount" of a pharmacologically active agent is intended to mean a nontoxic but sufficient amount of the agent, such that the desired prophylactic or therapeutic effect is produced. As will be pointed out below, the exact amount of a particular agent that is required will vary from subject to subject, depending on the species, age, and general condition of the subject, the severity of the condition being treated, the particular drug used and its mode of administration, and the like. Thus, it is not possible to specify an exact "effective amount" of any particular pharmacologically active agent. However, an appropriate effective amount may be determined for any particular drug by one of ordinary skill in the art using only routine experimentation.

By the term "pharmaceutically acceptable" to describe a carrier or excipient is meant a material which is not biologically or otherwise undesirable, i.e., the material may be administered along with the selected pharmacologically active agent without causing any undesirable biological effects or interacting in a deleterious manner with any of the other components of the pharmaceutical composition in which it is contained.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—$CH(CH_3)$—$CH_2$—], hexylene [—$(CH_2)_6$—] and the like. Preferred alkylene groups herein contain 1 to 12 carbon atoms. "Lower alkylene" refers to an alkylene group of 1 to 6, more preferably 1 to 4, carbon atoms.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 1 to 12 carbon atoms. The term "lower alkenyl" intends an alkenyl group of one to six carbon atoms, preferably one to four carbon atoms. The term "cycloalkenyl" intends a cyclic alkenyl group of three to eight, preferably five or six, carbon atoms.

The term "alkenylene" refers to a difunctional branched or unbranched hydrocarbon chain containing from 2 to 24 carbon atoms and at least one double bond. Preferred alkenylene groups herein contain 2 to 12 carbon atoms. "Lower alkenylene" refers to an alkenylene group of 2 to 6, more preferably 2 to 5, carbon atoms.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, t-butynyl, octynyl, decynyl and the like. Preferred alkynyl groups herein contain 1 to 12 carbon atoms. The term "lower alkynyl" intends an alkynyl group of one to six carbon atoms, preferably one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

"Halo" or "halogen" refers to fluoro, chloro, bromo or iodo, and usually relates to halo substitution for a hydrogen atom in an organic compound. Of the halos, chloro and fluoro are generally preferred.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

The Pharmaceutical Compositions of the Invention:

The present invention is premised on the discovery that covalent attachment of a pharmacologically active agent to a selective transthyretin ligand will provide pharmacokinetic properties similar to those of transthyretin or $T_4$. By varying the affinity of the ligand for transthyretin, the serum half-life of the pharmacologically active agent may be adjusted in either direction. It is generally preferred that the half-life of the drug will be significantly increased, typically by a factor of at least 10 and in some cases by a factor of 100 or more. This may be accomplished using ligands which bind strongly to transthyretin, i.e., with a $K_d$ in the range of approximately $10^{-5}$ to $10^{-10}$M, preferably at least about $10^{-7}$M, and most preferably at least about $10^{-8}$M.

The transthyretin-selective ligands of the invention, as noted above, preferably have binding affinities for thyroid-binding globulin and thyroid hormone receptor that are each less than about 1% of the binding affinity of the ligand for transthyretin. This ensures that the drug-carrying capacity of the ligand will be maximized without affecting free triiodothyronine or thyroxine levels or nuclear receptor binding. Preferred transthyretin-selective ligands are selected from the group consisting of those represented by structural formulae (I) through (IV)

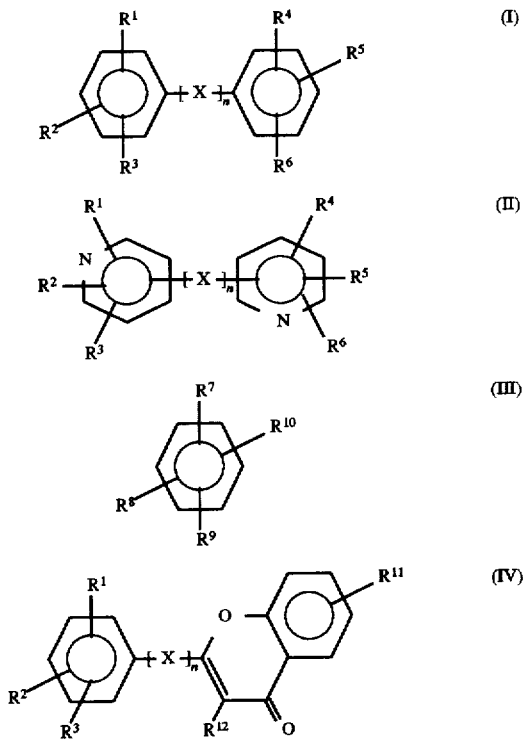

in which:

n is 0 or 1;

X is NH, O or lower alkylene optionally substituted with 1 to 4 substituents selected from the group consisting of lower alkyl, hydroxyl, carboxyl, halogen, amino, lower alkyl-substituted secondary amino, and lower alkyl-disubstituted tertiary amino, and, if lower alkylene, optionally containing 1 to 4 —O—, —NH—, —CONH— or —(CO)— linkages;

$R^1$, $R^2$, $R^3$, $R^4$, $R^5$, $R^6$, $R^7$, $R^8$, $R^9$, $R^{10}$ and $R^{11}$ are selected from the group consisting of hydrogen, halogen, halogen-substituted lower alkyl, hydroxyl, lower alkyl, cyano, —$(CH_2)_m$CHO, —$(CH_2)_m$OH, —$(CH_2)_m$COOR$^{13}$, and —$(CH_2)_m$CONHR$^{14}$ where m is 0 or 1, $R^{13}$ is hydrogen or $C_1$–$C_{12}$ alkyl, $C_1$–$C_{12}$ alkenyl or $C_1$–$C_{12}$ alkynyl optionally substituted with 1 to 8 substituents selected from the group consisting of hydroxyl, carboxyl, lower alkyl, halogen and amino, and optionally containing 1 to 8 —O—, —NH— or —(CO)— linkages, and $R^{14}$ is hydrogen or lower alkyl, with the proviso that at least one of $R^1$, $R^2$ and $R^3$ at least one of $R^4$, $R^5$ and $R^6$, and at least one of $R^7$, $R^8$, $R^9$ and $R^{10}$ is hydroxyl or —$(CH_2)_m$COOH; and $R^{12}$ is hydrogen or lower alkyl.

As may be deduced from the preceding definitions, preferred compounds of formulae (I) or (II) contain a hydroxyl or carboxyl group on each aromatic ring. Additionally, particularly preferred compounds of formulae (I) or (II) have at least one, and preferably two, halogen substituents on each aromatic ring, preferably iodine. As may be seen in the illustrative structures below, there are in some cases two halogen substituents each ortho to a hydroxyl substituent.

Preferred compounds of formula (III) also contain a hydroxyl or carboxyl group on the aromatic ring, as well as, preferably, at least one and preferably two or three halogen substituents.

Preferred compounds of formula (IV) similarly contain a hydroxyl or carboxyl group on the phenyl ring, as well as at least one, and preferably two, halogen substituents. $R^{11}$ is preferably hydroxyl, and $R^{12}$ is preferably lower alkyl.

Thus, examples of transthyretin-selective ligands include the following:

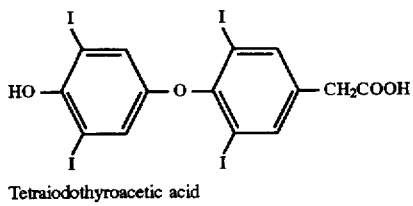

Tetraiodothyroacetic acid

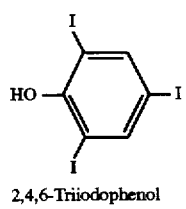

2,4,6-Triiodophenol

-continued
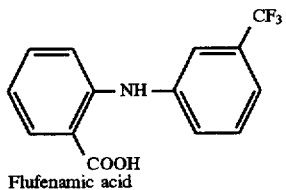
Flufenamic acid
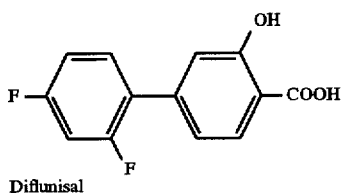
Diflunisal
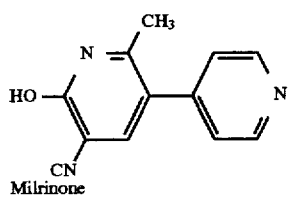
Milrinone
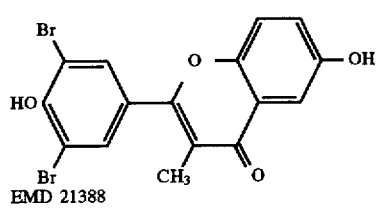
EMD 21388
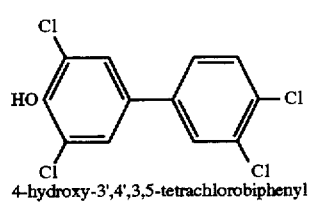
4-hydroxy-3',4',3,5-tetrachlorobiphenyl
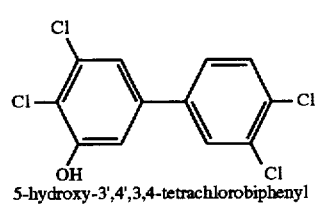
5-hydroxy-3',4',3,4-tetrachlorobiphenyl
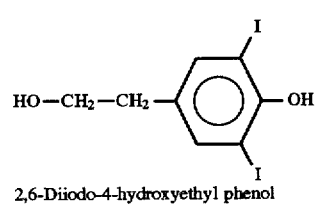
2,6-Diiodo-4-hydroxyethyl phenol
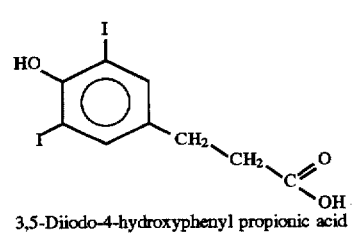
3,5-Diiodo-4-hydroxyphenyl propionic acid -continued
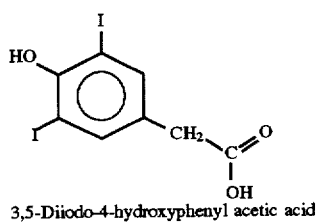
3,5-Diiodo-4-hydroxyphenyl acetic acid
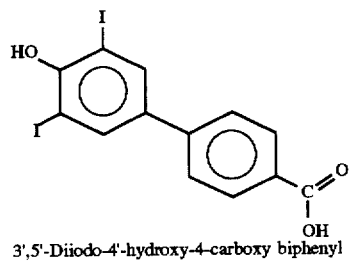
3',5'-Diiodo-4'-hydroxy-4-carboxy biphenyl
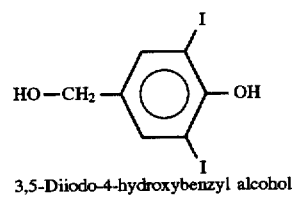
3,5-Diiodo-4-hydroxybenzyl alcohol
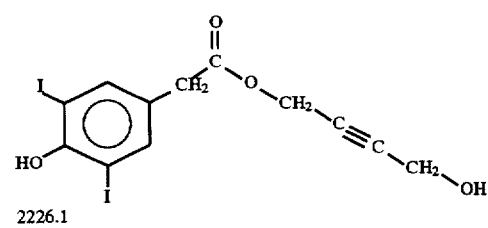
2226.1
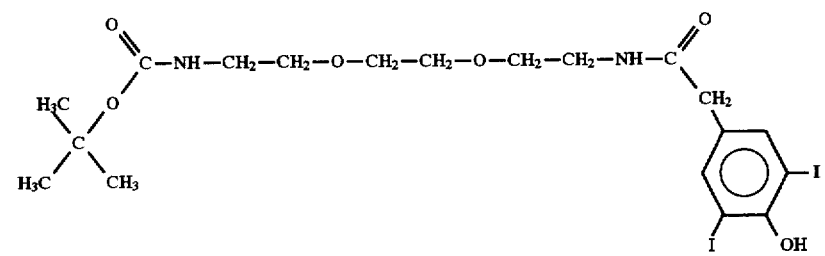
2051.1
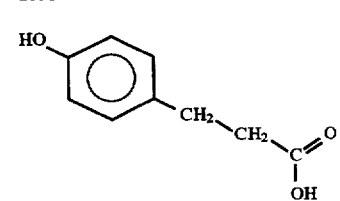
2227.1
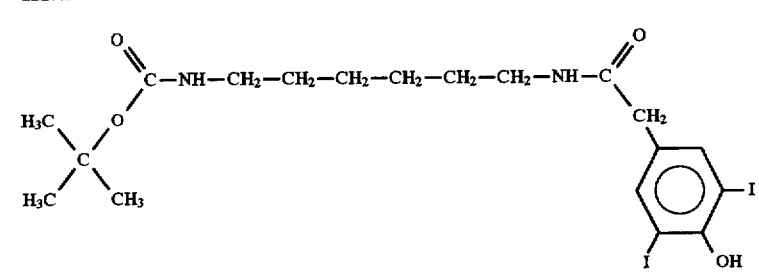

-continued 2049.1
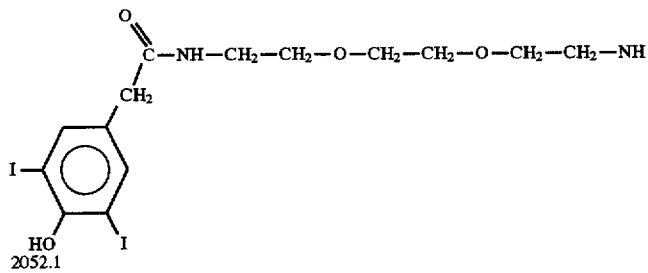
2052.1

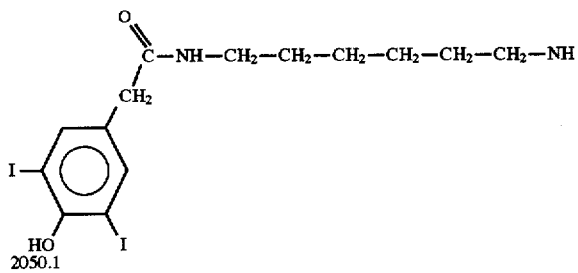
2050.1

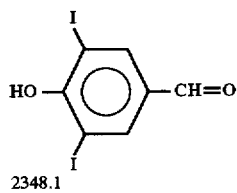
2348.1

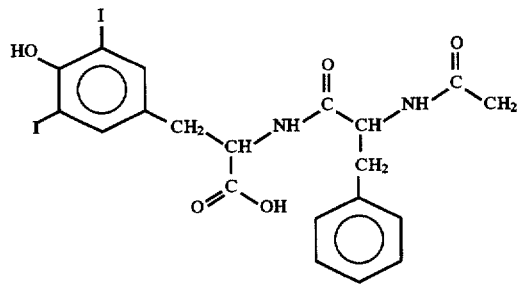
3260.1

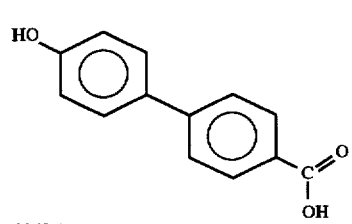
2349.1

As noted above, the compositions of the invention may be formulated using a wide variety of pharmacologically active agents. Preferred drugs for use in conjunction with the present invention are those which have a short half-life due primarily to renal excretion by glomerular filtration and not to metabolism or active transport pathways; preferably, at least about 50% of the drug is cleared through urinary excretion and less than about 10% of the drug metabolized and/or actively transported. Additionally, the plasma binding of the drug should be less than about 50% as measured using conventional techniques. Also, clearly, the drug should be capable of derivatization as described herein without significant loss of activity. It will be appreciated by those skilled in the art that drugs may be readily screened using the aforementioned criteria and a determination then made as to whether the drug would be useful in conjunction with the present invention. Particularly preferred drugs which meet the aforementioned requirements are acyclovir, amoxicillin, ampicillin, arginine vasopressin (and its analogs, e.g., dDAVP), azlocillin, captopril, carbenicillin, ceflacor, cefadroxil, cefamandole, cephaloxin, cilastatin, cimetidine, dideoxyinosine, d4T, endothelin, famotidine, imipenem, insulin, β-interferon, interleukin-2, lidocaine, nizatidine, octreotide, procainamide, N-acetyl-procainamide, ranitidine, nizatidine, saralasin, superoxide dismutase, ticarcillin and zidovudine.

After having selected the agent to be administered using the criteria outlined above, conjugates are formed by covalent bonding of the selected drug to the transthyretin selective ligand. The drug is caused to bind through a functional group or side-chain which is not essential for pharmacological activity, to a similarly nonessential portion of the selected transthyretin ligand. It will be appreciated that such "nonessential" regions may be readily determined by those skilled in the art. While any number of covalent linkages may be envisioned, the following are representative functional groups which may be present on the drug and the TTR ligand to provide for covalent linkages:

| DRUG | TTR Ligand | Linkage |
|---|---|---|
| R—NH$_2$ | R'—COOH | R—NH—(CO)—R' |
| R—OH | R'-halogen | R—O—R' |
| R—SH | R'-halogen | R—S—R' |
| R—COOH | R—NH$_2$ | R—(CO)—NH—R' |
| R—COOH | R'OH | RCOOR' |
| R—COOH | R'SH | RCOSR' |

R and R' represent those portions of the drug and transthyretin ligand, respectively, which are not illustrated. Reaction between the functional groups on the drug and TTR ligand may be effected using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992), the disclosure of which is hereby incorporated by reference. One example of a suitable complexation technique is that described in U.S. Pat. Nos. 4,766,106 to Katre et al. and 4,902,502 to Nitecki et al., the disclosures of which are hereby incorporated by reference; that method involves conjugation of a protein (IL-2 in the aforementioned patents) to polyethylene glycol or a polyoxyethylated polyol by binding free amino groups present on the protein, normally in lysine residues, to a terminal anhydride of a linking moiety (in turn bound to the polyethylene glycol or polyoxyethylated polyol). Reaction between the anhydride and the free amino group produces an amide bond. See also Tae, "Bifunctional Reagents" in *Methods in Enzymology* 91:580–595 (1983), also incorporated by reference, which describes the use of N-hydroxysuccinimide (NHS) esters as coupling agents, reacting with free amine groups present on the moiety to be "coupled." These techniques may be used in the present case to bind free amino groups present on a drug, e.g., extending from lysine residues in a peptide drug, to a linker-bound anhydride with the opposing end of the linker bound to the transthyretin ligand.

An example of covalent conjugates prepared in this way thus includes the following:

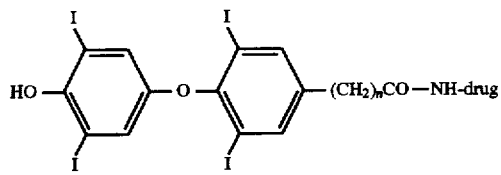

-continued

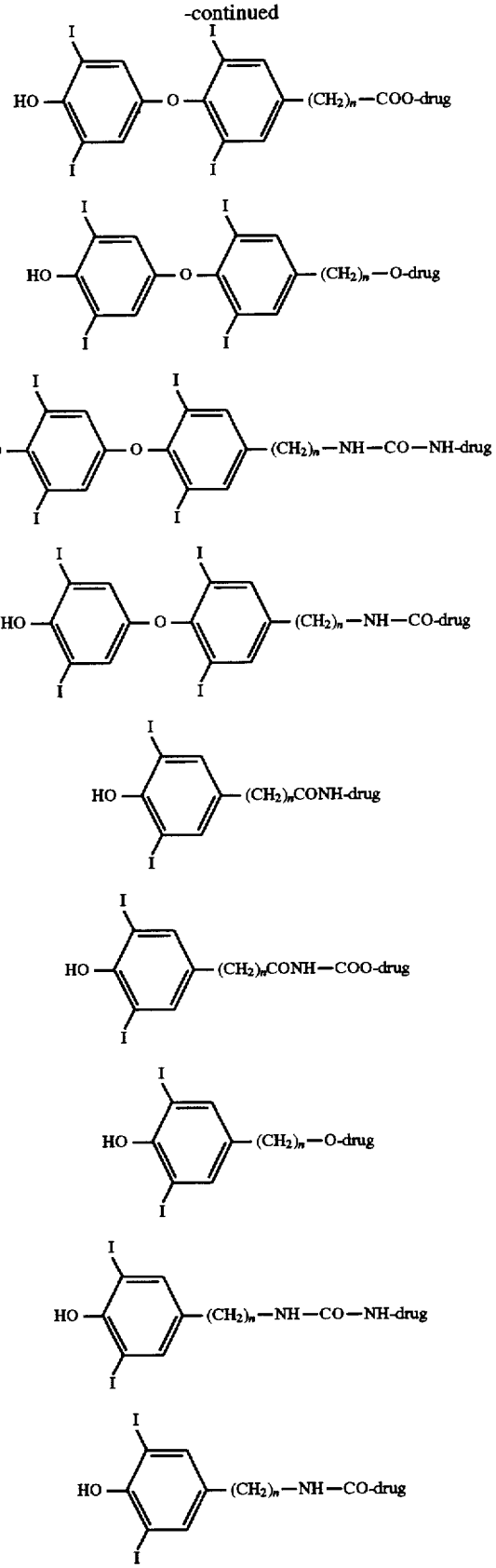

In some cases, the pharmacologically active agent may not contain a functional group capable of providing the necessary linkage to the TTR ligand. It will then be necessary, in some cases, to modify the pharmacologically active agent so that it contains a functional group. It will be appreciated that techniques for modifying drugs in this way will be known to or readily deduced by those skilled in the art.

Utility and Administration

The pharmaceutical compositions of the invention may contain, in addition to a therapeutically effective amount of the drug-ligand conjugates described above, pharmaceutically acceptable carriers, medicinal agents, adjuvants, diluents, etc. *Remington's Pharmaceutical Sciences*, 18th edition, by E. W. Martin (Mack Publ. Co., Easton Pa.) discloses typical carriers, adjuvants, diluents and the like, and methods of preparation known in the art.

The compositions may be administered orally, parenterally (e.g., intravenously), by intramuscular injection, by intraperitoneal injection, as suppositories, or the like. Oral administration is preferred. The amount of active compound administered will, of course, be dependent on the subject being treated, the subject's weight, the manner of administration and the judgment of the prescribing physician. Information concerning dosages of various pharmacological agents may be found in standard pharmaceutical reference books, e.g., *Remington's Pharmaceutical Sciences*, cited above.

The pharmaceutical compositions may be in the form of solid, semi-solid or liquid dosage forms, such as, for example, tablets, pills, capsules, powders, liquids, suspensions, or the like, preferably in unit dosage form suitable for single administration of a precise dosage.

An additional utility for the drug-ligand conjugates of the invention derives from the use of labeled drugs, i.e., drugs which are covalently or otherwise bound to a detectable label. Such conjugates by virtue of their selectivity for transthyretin and the presence of a detectable label (such as a fluorescent moiety or the like), are useful in an assay wherein transthyretin is to be quantitated.

Experimental

The following examples are put forth so as to provide those of ordinary skill in the art with a complete disclosure and description of how to prepare the present pharmaceutical compositions, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLE 1

Ligand Preparation

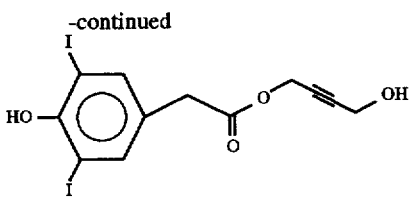

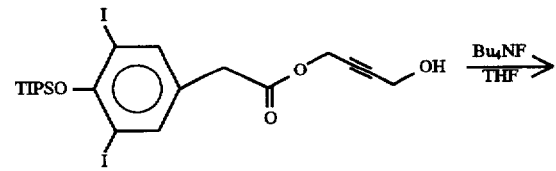

To a solution of the TIPS (tetraiodophthalein sodium) protected phenolic compound shown above in 8 mL THF was added 0.35 g $Bu_4NF \cdot XH_2O$. The solution was stirred at room temperature for 2 hours.

The solvent was removed, and the residue dissolved in 1 mL $H_2O$ and 10 mL ethyl acetate. It was washed three times with 5 mL $H_2O$ and dried over $Na_2SO_4$. Removal of the drying agent and solvent gave 0.14 g product. The identity of the product was confirmed by NMR and mass spectroscopy.

(b.)

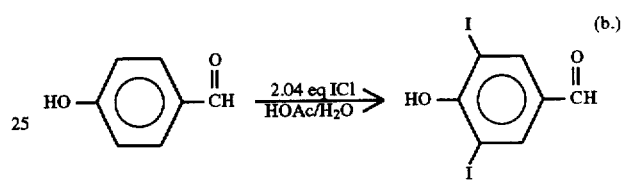

9.23 g ICl was transferred to a 500 mL round bottom flask equipped with a stopper rubber. 75 mL acetic acid was added under argon, followed by addition of 3.39 g 4-hydroxybenzaldehyde. The mixture was stirred at room temperature for 5 minutes and at 45° C. for 10 minutes. It was then allowed to cool to room temperature and stirred overnight.

1 g $NaHSO_3$ in 50 mL $H_2O$ was added, and the brown reaction mixture turned yellow. It was filtered under vacuum, the solid was redissolved in ethanol, and then recrystallized from ethanol and $H_2O$. 3.17 g product was obtained. The identity of the product was confirmed by NMR and mass spectroscopy.

(c.)

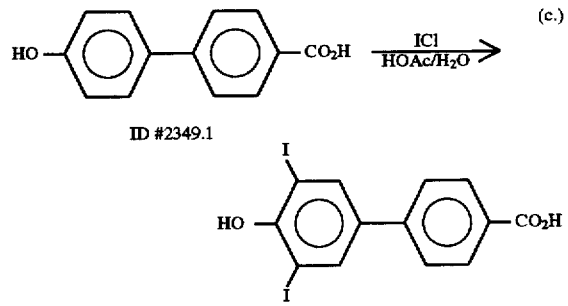

ID #2349.1

2.30 g ICl was transferred to a round bottom flask in a hood and then dissolved in 25 mL glacial acetic acid. A solution of 1.37 g p-hydroxyphenylbenzoic acid in 25 mL glacial acetic acid was then added to the ICl solution at 60° C. After the mixture was stirred at room temperature for 5 minutes, 100 mL $H_2O$ was added, and the mixture was again stirred at 60° C. for 2 hours. 1 g $NaHSO_3$ in 25 mL $H_2O$ was added, and the mixture was stirred at room temperature for 10 minutes. The precipitate was filtered through a frit glass funnel, and the solid was then dissolved in hot ethanol and crystallized from ethanol/$H_2O$. The product was recrystallized with ethanol and aqueous $NaHSO_3$ solution. Approximately 800 mg solid was obtained, the identity of which was confirmed by NMR and mass spectroscopy.

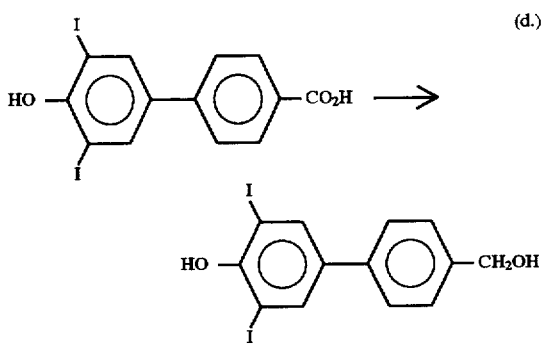
(d.)

Removal of drying agent and solvent gave approximately 700 g crude compound.

The crude product was chromatographed on $SiO_2$ with hexane/ethyl acetate (60:40) to give two fractions "A" and "B."

Fraction B was partially dissolved in 3N NaOH, washed once with ether/hexane (50:50), reacidified to pH~4 with 10% citric acid, and then extracted two times with ethyl acetate. The combined ethyl acetate layer was dried over $Na_2SO_4$. Removal of $Na_2SO_4$ and solvent gave approximately 10 mg oil.

The original ether/hexane (50/50) layer was washed with 3N NaOH. The aqueous layer was acidified with 10% citric acid to pH~4 and extracted two times with ethyl acetate. The combined ethyl acetate layers were dried over $Na_2SO_4$. Removal of solids and solvent gave approximately 10 mg solid. The identity of the product was confirmed by NMR and mass spectroscopy.

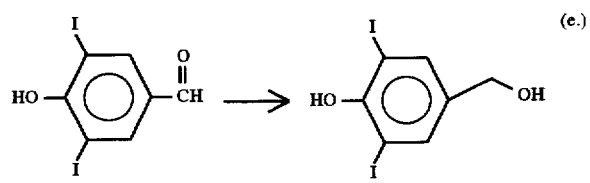
(e.)

To a solution of 0.82 g aldehyde (shown above) in 6 mL THF was added 2 mL 1M $BH_3$ in THF. The mixture was stirred under argon at room temperature for three hours. Solvent was then removed, the residue was dissolved in ethyl acetate, washed two times with $H_2O$, and dried over $Na_2SO_4$. Removal of solvent and solids gave approximately 300 mg crude product.

The 300 mg crude product was chromatographed on $SiO_2$ with ethyl acetate/hexane (40/60) to give three hours. Solvent was then removed, the residue was dissolved in ethyl acetate, washed two times with $H_2O$, and dried over $Na_2SO_4$. Removal of solvent and solids gave approximately 300 mg crude product.

The 300 mg crude product was chromatographed on $SiO_2$ with ethyl acetate/hexane (40/60) to give three fractions. Only the first fraction was found to be the desired product, as confirmed by NMR and mass spectroscopy.

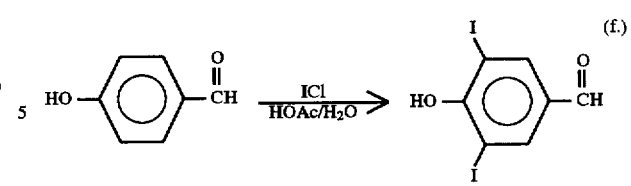
(f.)

25.22 g ICl was transferred to a 500 mL round bottom flask equipped with a nonrubber stopper, under a hood. 150 mL acetic acid was then added under argon, followed by addition of 7.59 g 4-hydroxybenzaldehyde in a single portion. The mixture was stirred at room temperature for a few minutes until all aldehyde dissolved. 150 mL $H_2O$ was added. The mixture was stirred at 45° C. for 10 minutes, then allowed to cool to room temperature and stirred overnight.

1.5 g $NaHSO_3$ was added with 100 mL $H_2O$, and the mixture stirred under argon until no further color changes were observed. The solid/liquid mixture was filtered through a frit glass funnel, and the solid so obtained was dissolved in ethanol and recrystallized from an ethanol/$H_2O$ mixture. The solvent was filtered off quickly, and the solid product was washed with ethanol and dried overnight under vacuum. 19 g crude product was obtained. The identity of the product was confirmed by NMR and mass spectroscopy.

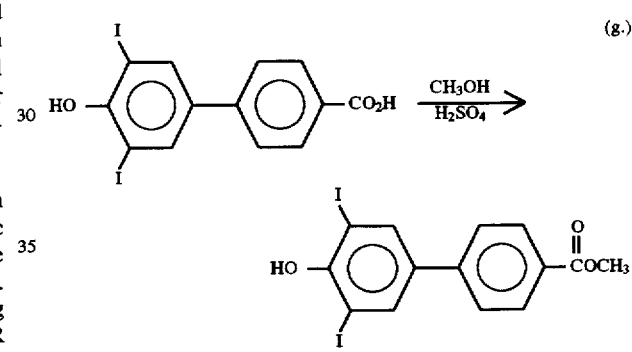
(g.)

To a round bottom flask containing 7 mL $CH_3OH$ was added 4 drops of concentrated $H_2SO_4$ with cooling. Then 22 mg acid starting material (shown above) was added and the mixture was refluxed for one hour. Solvent was removed and the residue was dissolved in ethyl acetate, washed 2X with 5% $NaHCO_3$, and dried over $Na_2SO_4$. Removal of solvent and drying agent gave 0.01 g crude product.

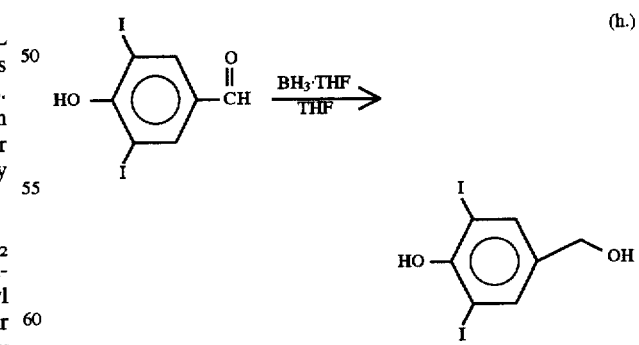
(h.)

To a solution of 3.10 g aldehyde (shown above) in 10 mL THF under argon was added 10 mL $BH_3·THF$ at 0° C. over a 10 minute period. The mixture was stirred under argon at 0° C. for 30 minutes, and then stirred at room temperature for 3 hours.

The solvent was removed and the residue was dissolved in ethyl acetate, washed two times with 5% $NaHCO_3$, once with 5% NaCl, and then dried over $Na_2SO_4$. Removal of solids and solvent gave 3.14 g crude product, which was further dried under vacuum. The identity of the product was confirmed by NMR and mass spectroscopy.

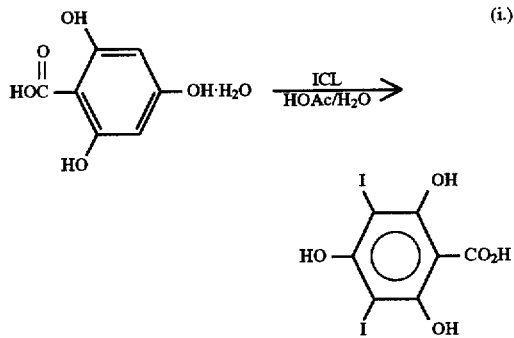

(i.)

To a 500 mL round bottom flask equipped with a plastic stopper was transferred 20.10 g ICl under a fume hood. 60 mL acetic acid was then added, followed by the addition of 3.50 g 2,4,6-trihydroxylbenzoic acid. The mixture was refluxed under an argon balloon overnight. 100 mL $H_2O$ was added and the mixture was refluxed for another two hours. 6 g $NaHSO_3$ was added while the mixture was stirred. 10% $NaHSO_3$ aqueous solution was then added until no further color changes were observed.

The solvent was removed, and the residue was crystallized from ethanol and $H_2O$ and then recrystallized from ethanol. 1.42 g solid product was obtained after high vacuum drying. The identity of the product was confirmed by mass spectroscopy.

EXAMPLE 2

The procedure of R. Somack et al., "Molecular interactions of toxic chlorinated dibenzo-p-dioxins and dibenzofurans with thyroxine binding prealbumin," *J. Med. Chem.* 28:375–381 (1985), was followed to evaluate the efficacy of a number of TTR ligands which can be used to prepare the drug-ligand conjugates of the invention. Results are set forth in the following table, wherein "%$T_4$" represents the percent inhibition of radiolabelled $T_4$ binding to TTR".

| Compound | ~% T4 | [I] |
|---|---|---|
| | 40 | 10 uM |
| | 25 | 10 uM |
| | 15 | 10 uM |
| | 80 | 1 uM |

-continued

| Compound | ~% T4 | [I] |
|---|---|---|
| 2,6-diiodo-4-(hydroxymethyl)phenol | 70 | 1 uM |
| 2,4,6-triiodophenol | 90 | 10 uM |
| 3,3',5,5'-tetraiodo-4'-hydroxydiphenyl ether-4-acetic acid | 90 | 10 uM |
| 4-hydroxybut-2-ynyl [3,5-diiodo-4-hydroxyphenyl]acetate | 90 | 10 uM |
| 3,5-diiodo-4-(2-hydroxyethyl)phenol | 85 | 10 uM |
| 3-(3,5-diiodo-4-hydroxyphenyl)propionic acid | 80 | 10 uM |
| (3,5-diiodo-4-hydroxyphenyl)acetic acid | 70 | 10 uM |
| Boc-NH-CH₂-CH₂-O-CH₂-CH₂-O-CH₂-CH₂-NH-C(O)-CH₂-(3,5-diiodo-4-hydroxyphenyl) | 45 | 10 uM |

We claim:

1. A pharmaceutical composition comprising a covalent conjugate of a pharmacologically active agent and a transthyretin-selective ligand whose binding affinities for thyroid-binding globulin and thyroid hormone receptor are each less than about 1% that of the binding affinity of said ligand for transthyretin, wherein the transthyretin-selective ligand is selected from the group consisting of the following structural formulae (I), (II) and (IV):

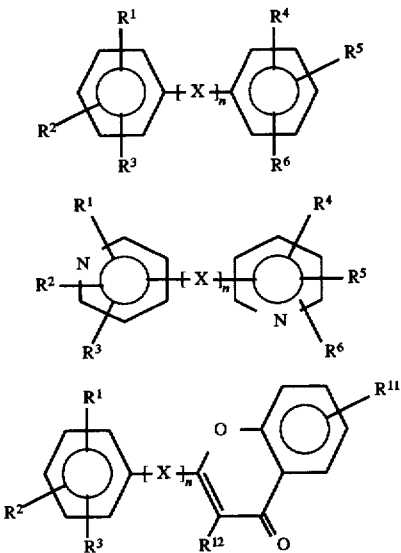

wherein:

n is 0 or 1;

X is NH, O or lower alkylene optionally substituted with 1 to 4 substituents selected from the group consisting of lower alkyl, hydroxyl, carboxyl, halogen, amino, lower alkyl-substituted secondary amino, and lower alkyl-disubstituted tertiary amino and, if lower alkylene, optionally containing 1 to 4 —O—, —NH—, —CONH— or —(CO)— linkages;

$R^1$, $R^2$, $R^3$, $R^4$, $R^5$, $R^6$, and $R^{11}$ are selected from the group consisting of hydrogen, halogen, halogen-substituted lower alkyl, hydroxyl, lower alkyl, cyano, —$(CH_2)_m$CHO, —$(CH_2)_m$OH, —$(CH_2)_m$ $COOR^{13}$, and —$(CH_2)_m$CONHR$^{14}$ wherein m is 0 or 1, $R^{13}$ is hydrogen or $C_1$-$C_{12}$ alkyl, $C_1$-$C_{12}$ alkenyl or $C_1$-$C_{12}$ alkynyl, and, when $R^{13}$ is other than hydrogen, it is optionally substituted with 1 to 8 substituents selected from the group consisting of hydroxyl, carboxyl, lower alkyl, halogen and amino, and further optionally contains 1 to 8 —O—, —NH—, or —(CO)— linkages, and $R^{14}$ is hydrogen or lower alkyl, with the proviso that at least one of $R^1$, $R^2$ and $R^3$, and at least one of $R^4$, $R^5$ and $R^6$ is hydroxyl or —$(CH_2)_m$COOH; and $R^{12}$ is hydrogen or lower alkyl.

2. The pharmaceutical composition of claim 1, wherein the pharmacologically active agent is selected such that following administration to a mammalian individual, at least about 50% of the agent is cleared through urinary excretion and less than 10% of the agent is metabolized or actively transported.

3. The pharmaceutical composition of claim 2, wherein the pharmacologically active agent is further selected such that following administration to a mammalian individual, the plasma binding of the drug is less than about 50%.

4. The pharmaceutical composition of claim 1, wherein the transthyretin-selective ligand has the structural formula (I).

5. The pharmaceutical composition of claim 1, wherein the transthyretin-selective ligand is tetraiodothyroacetic acid.

6. The pharmaceutical composition of claim 4, wherein the transthyretin-selective ligand is flufenamic acid.

7. The pharmaceutical composition of claim 4, wherein the transthyretin-selective ligand is diflunisal.

8. The pharmaceutical composition of claim 1, wherein the transthyretin-selective ligand has the structural formula (II).

9. The pharmaceutical composition of claim 8, wherein the transthyretin-selective ligand is milrinone.

10. The pharmaceutical composition of claim 1, wherein the transthyretin-selective ligand has the structural formula (IV).

11. The pharmaceutical composition of claim 10, wherein the transthyretin-selective ligand is EMD 21388.

12. The pharmaceutical composition of claim 1, wherein the pharmacologically active agent is a peptide drug or a fragment thereof.

13. The pharmaceutical composition of claim 1, wherein the pharmacologically active agent is selected from the group consisting of acyclovir, amoxicillin, ampicillin, arginine vasopressin, azlocillin, captopril, carbenicillin, ceflacor, cefadroxil, cefamandole, cephaloxin, cilastatin, cimetidine, dideoxyinosine, d4T, endothelin, famotidine, imipenem, insulin, β-interferon interleukin-2, lidocaine, nizatidine, octreotide, procainamide, N-acetyl-procainamide, ranitidine, nizatidine, saralasin, superoxide dismutase, ticarcillin and zidovudine.

14. A method for extending the half-life of a pharmacologically active agent containing a functional group not essential for pharmacological activity, comprising covalently binding said agent, through said functional group, to a transthyretin-selective ligand whose binding affinities for thyroid-binding globulin and thyroid hormone receptor are each less than about 1% that of the binding affinity of said ligand for transthyretin.

15. The method of claim 14, wherein the transthyretin-selective ligand is selected from the group consisting of the following structural formulae (I) through (IV):

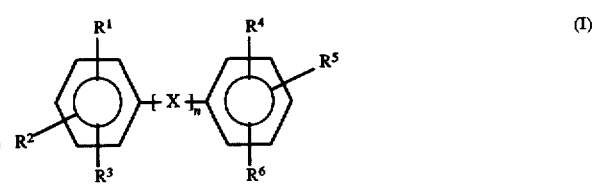

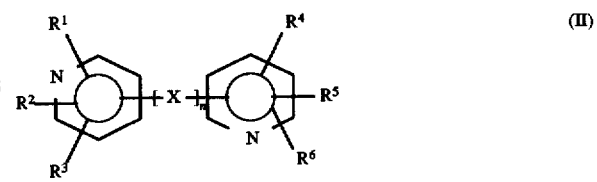

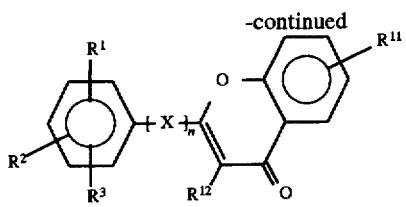

(IV)

wherein:

n if 0 or 1;

X is NH, O or lower alkylene optionally substituted with 1 to 4 substituents selected from the group consisting of lower alkyl, hydroxyl, carboxyl, halogen, amino, lower alkyl-substituted secondary amino, and lower alkyl-disubstituted tertiary amino and, if lower alkylene, optionally containing 1 to 4 —O—, —NH—, —CONH— or —(CO)— linkages;

$R^1$, $R^2$, $R^3$, $R^4$, $R^5$, $R^6$, $R^7$, $R^8$, $R^9$, $R^{10}$ and $R^{11}$ are selected from the group consisting of hydrogen, halogen, halogen-substituted lower alkyl, hydroxyl, lower alkyl, cyano, —$(CH_2)_m$CHO, —$(CH_2)_m$OH, —$(CH_2)_m$COOR$^{13}$, and —$(CH_2)_m$CONHR$^{14}$ where m is 0 or 1, $R^{13}$ is hydrogen or $C_1$–$C_{12}$ alkyl, $C_1$–$C_{12}$ alkenyl or $C_1$–$C_{12}$ alkynyl and, when $R^{13}$ is other than hydrogen, it is optionally substituted with 1 to 8 substituents selected from the group consisting of hydroxyl, carboxyl, lower alkyl, halogen and amino, and optionally containing 1 to 8 —O—, —NH— or —(CO)— linkages, and $R^{14}$ is hydrogen or lower alkyl, with the proviso that at least one of $R^1$, $R^2$ and $R^3$, at least one of $R^4$, $R^5$ and $R^6$, and at least one of $R^7$, $R^8$, $R^9$ and $R^{10}$ is hydroxyl or —$(CH_2)_m$COOH; and $R^{12}$ is hydrogen or lower alkyl.

16. The method of claim 15, wherein the transthyretin-selective ligand has the structural formula (I).

17. The method of claim 16, wherein the transthyretin-selective ligand is tetraiodothyroacetic acid.

18. The method of claim 16, wherein the transthyretin-selective ligand is flufenamic acid.

19. The method of claim 16, wherein the transthyretin-selective ligand is diflunisal.

20. The method of claim 15, wherein the transthyretin-selective ligand has the structural formula (II).

21. The method of claim 20, wherein the transthyretin-selective ligand is milrinone.

22. The method of claim 15, wherein the transthyretin-selective ligand has the structural formula (III).

23. The method of claim 22, wherein the transthyretin-selective ligand is 2,4,6-triiodophenol.

24. The method of claim 15, wherein the transthyretin-selective ligand has the structural formula (IV).

25. The method of claim 24, wherein the transthyretin-selective ligand is EMD 21388.

26. The method of claim 14, wherein the pharmacologically active agent is a peptide drug or a fragment thereof.

27. The method of claim 14, wherein the pharmacologically active agent is selected from the group consisting of acyclovir, amoxicillin, ampicillin, arginine vasopressin, azlocillin, captopril, carbenicillin, ceflacor, cefadroxil, cefamandole, cephaloxin, cilstatin, cimetidine, dideoxyinosine, d4T, endothelin, famotidine, imipenem, insulin, β-interferon interleukin-2, lidocaine, nizatidine, octreotide, procainamide, N-acetyl-procalnamide, ranitidine, nizatidine, saralasin, superoxide dismutase, ticarcillin and zidovudine.

* * * * *